(12) United States Patent
Wu

(10) Patent No.: US 12,115,291 B2
(45) Date of Patent: Oct. 15, 2024

(54) ELECTRIC HEATING FRAGRANCE DIFFUSER

(71) Applicant: Pro-Iroda Industries, Inc., Taichung (TW)

(72) Inventor: Wei Cheng Wu, Taichung (TW)

(73) Assignee: PRO-IRODA INDUSTRIES, INC., Taichung (TW)

( * ) Notice: Subject to any disclaimer, the term of this patent is extended or adjusted under 35 U.S.C. 154(b) by 610 days.

(21) Appl. No.: 17/382,546

(22) Filed: Jul. 22, 2021

(65) Prior Publication Data

US 2022/0184263 A1    Jun. 16, 2022

(30) Foreign Application Priority Data

Dec. 16, 2020   (TW) .................................. 109144573

(51) Int. Cl.
*A61L 9/03*    (2006.01)
(52) U.S. Cl.
CPC ........... *A61L 9/03* (2013.01); *A61L 2209/133* (2013.01)
(58) Field of Classification Search
CPC .. A61L 9/03; A61L 2209/133; A61L 2209/15; A61M 11/042; A61M 2205/8206
See application file for complete search history.

(56) References Cited

U.S. PATENT DOCUMENTS

| | | |
|---|---|---|
| 5,392,379 A | 2/1995 | Fussell |
| 8,668,885 B2 | 3/2014 | Wirz |
| 8,938,159 B2 | 1/2015 | Hsiao |
| 8,974,107 B2 | 3/2015 | Hsiao |
| 9,028,759 B2 | 5/2015 | Wirz |
| 9,109,780 B2 | 8/2015 | Hsiao |
| 9,206,963 B2 | 12/2015 | Hsiao |
| 9,410,695 B2 | 8/2016 | Hsiao |
| 9,498,553 B2 | 11/2016 | Hsiao et al. |
| 9,500,358 B2 | 11/2016 | Hsiao |
| 9,844,609 B2 | 12/2017 | Hsiao |
| 10,064,969 B2 | 9/2018 | Hsiao |
| 10,842,901 B2 * | 11/2020 | Hsiao ........................ A61L 9/03 |
| 11,369,709 B2 | 6/2022 | Hsiao |

(Continued)

FOREIGN PATENT DOCUMENTS

| | | |
|---|---|---|
| CN | 206391238 U | 8/2017 |
| CN | 208942985 U | 6/2019 |

(Continued)

*Primary Examiner* — Maris R Kessel
*Assistant Examiner* — Brendan A Hensel
(74) *Attorney, Agent, or Firm* — MUNCY, GEISSLER, OLDS & LOWE, P.C.

(57) ABSTRACT

An electric heating fragrance diffuser includes a hollow body and a fragrance diffusing device. A power source and an electric wire are arranged in the body. The fragrance diffusing device includes a fragrance holder, a fragrance box, and an electric heating plate. The fragrance holder is disposed in the body and provided with a first hole communicating with upper and lower edges of the fragrance holder in a vertical direction. The upper edge of the fragrance holder is recessed with a fragrance groove surrounding the first hole. The fragrance box is detachably arranged in the fragrance groove. The electric heating plate is connected to the lower edge of the fragrance holder and provided with a second hole aligned with the first hole.

3 Claims, 4 Drawing Sheets

(56) References Cited

U.S. PATENT DOCUMENTS

| | | |
|---|---|---|
| 2008/0130266 A1 | 6/2008 | DeWitt et al. |
| 2014/0014736 A1 | 1/2014 | Wirz |
| 2014/0072286 A1* | 3/2014 | Hsiao ..................... A61L 9/03 |
| | | 392/390 |
| 2014/0110389 A1 | 4/2014 | Hsiao |
| 2015/0109823 A1 | 4/2015 | Hsiao |
| 2015/0117056 A1 | 4/2015 | Hsiao |
| 2015/0283280 A1 | 10/2015 | Belongia |
| 2016/0195257 A1 | 7/2016 | Hsiao |
| 2017/0128608 A1 | 5/2017 | Hsiao |
| 2018/0064839 A1 | 3/2018 | Hsiao |
| 2018/0126022 A1 | 5/2018 | Hsiao |
| 2018/0228930 A1* | 8/2018 | Davis ..................... A61L 9/032 |
| 2019/0022266 A1 | 1/2019 | Hsiao |
| 2019/0022267 A1 | 1/2019 | Hsiao |
| 2019/0022268 A1 | 1/2019 | Hsiao |
| 2020/0171191 A1 | 6/2020 | Hsiao |
| 2020/0222571 A1 | 7/2020 | Hsiao |

FOREIGN PATENT DOCUMENTS

| | | |
|---|---|---|
| EP | 3572098 A1 | 11/2019 |
| JP | H0556017 U | 7/1993 |
| WO | 2018152058 A1 | 8/2018 |

\* cited by examiner

ELECTRIC HEATING FRAGRANCE DIFFUSER

BACKGROUND OF THE INVENTION

The present invention relates to a fragrance diffuser, and particularly to an electric heating fragrance diffuser.

Typical combustion devices capable of emitting fragrance include a burner and a fragrance apparatus. The burner is provided with a top end having a burning portion. The fragrance apparatus includes a placing frame and a fragrance box. The placing frame is disposed at the top end and is provided with an inner wall and an outer wall. The inner wall extends in a vertical direction and is wrapped around the burning portion. The outer wall extends in the vertical direction and surrounds the outer side of the inner wall in a horizontal direction. An accommodating space is arranged between the inner wall and the outer wall. The fragrance box is disposed in the accommodating space.

However, the combustion device generates heat by burning fuel, which may be dangerous if the user operates carelessly, and the structure is complicated.

In view of the above, a need exists for a novel fragrance diffuser that mitigates and/or obviates the above drawbacks.

BRIEF SUMMARY OF THE INVENTION

An electric heating fragrance diffuser according to the present invention includes a body and a fragrance diffusing device. The body is hollow and provided with an accommodating space inside. A power source and an electric wire are arranged in the accommodating space. The fragrance diffusing device includes a fragrance holder, a fragrance box, and an electric heating plate. The fragrance holder is disposed in the accommodating space and defines upper and lower edges in a vertical direction. The fragrance holder is provided with a first hole communicating with upper and lower edges of the fragrance holder. The upper edge of the fragrance holder is recessed with a fragrance groove surrounding the first hole. The fragrance box is detachably arranged in the fragrance groove. The electric heating plate is connected to the lower edge of the fragrance holder and provided with a second hole aligned with the first hole.

In an example, the fragrance diffusing device is provided with a bottom plate securely connected to the lower edge of the fragrance holder. The electric heating plate is disposed between the fragrance holder and the bottom plate.

In an example, the body defines upper and lower edges in a vertical direction. The upper edge of the body is provided with a top face connected to the accommodating space. The fragrance diffusing device includes a supporting frame mounted around the fragrance holder. An outer periphery of the supporting frame abuts against the top face.

In an example, the supporting frame defines upper and lower edges in a vertical direction. The upper edge of the supporting frame is provided with a plurality of lugs. The fragrance diffusing device includes a windshield abutted against the plurality of lugs and not in contact with the body and the fragrance holder.

In an example, the fragrance diffusing device includes a top cover connected to the upper edge of the fragrance holder. The top cover is provided with a third hole aligned with the first hole and a plurality of aeration holes aligned with the fragrance groove.

In an example, the lower edge of the body is provided with a bottom face connected to the accommodating space opposite to the top face and adjacent to the power source. An end of the accommodating space connecting with the bottom face forms two air hole respectively located at two opposite sides of the power source. The bottom face convexly provided with a plurality of feet in a direction opposite to the top face.

The present invention will become clearer in light of the following detailed description of illustrative embodiments of this invention described in connection with the drawings.

DETAILED DESCRIPTION OF THE INVENTION

Figure 1:
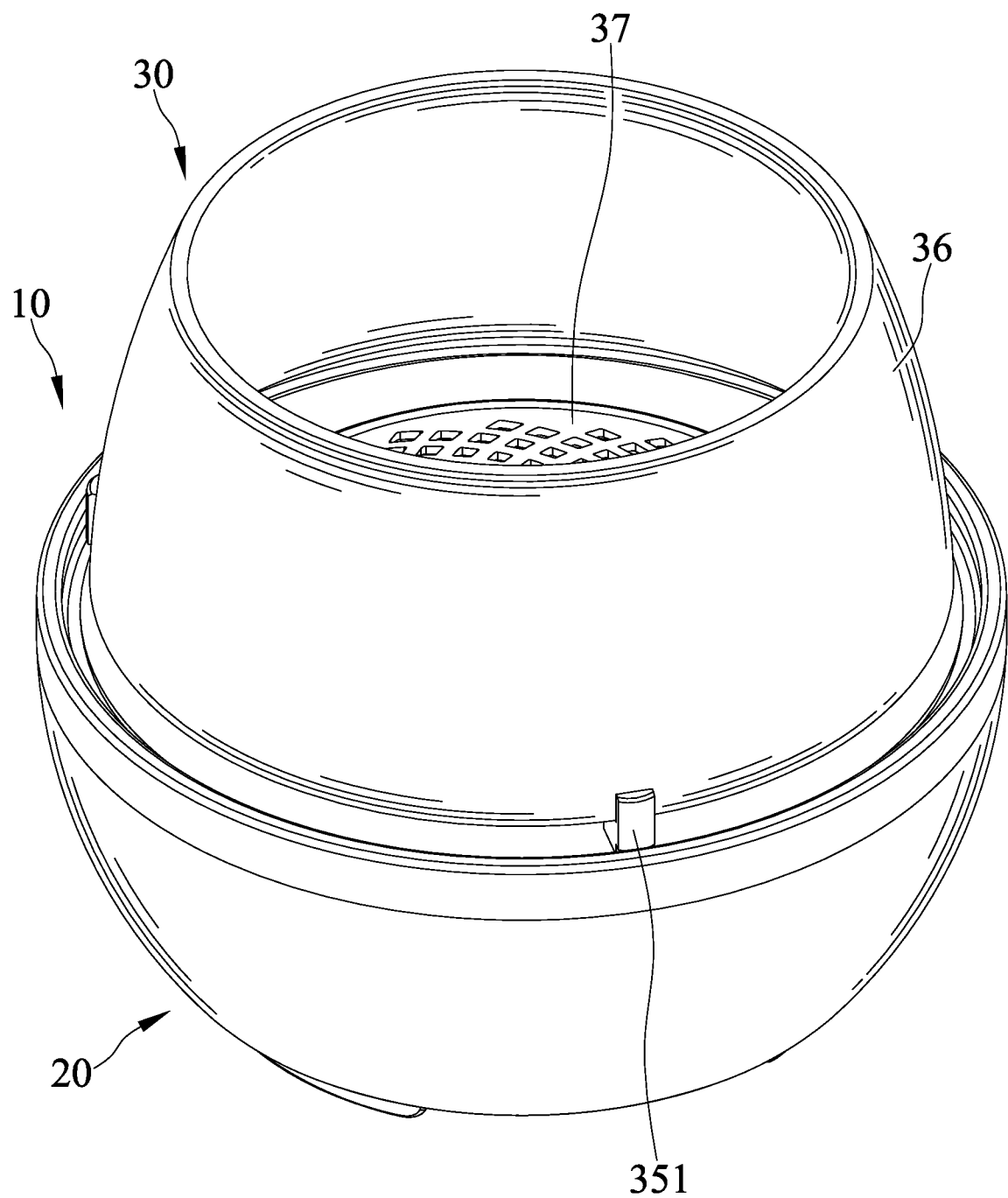
FIG. 1 is a perspective view of an electric heating fragrance diffuser of an embodiment according to the present invention.
Figure 2:
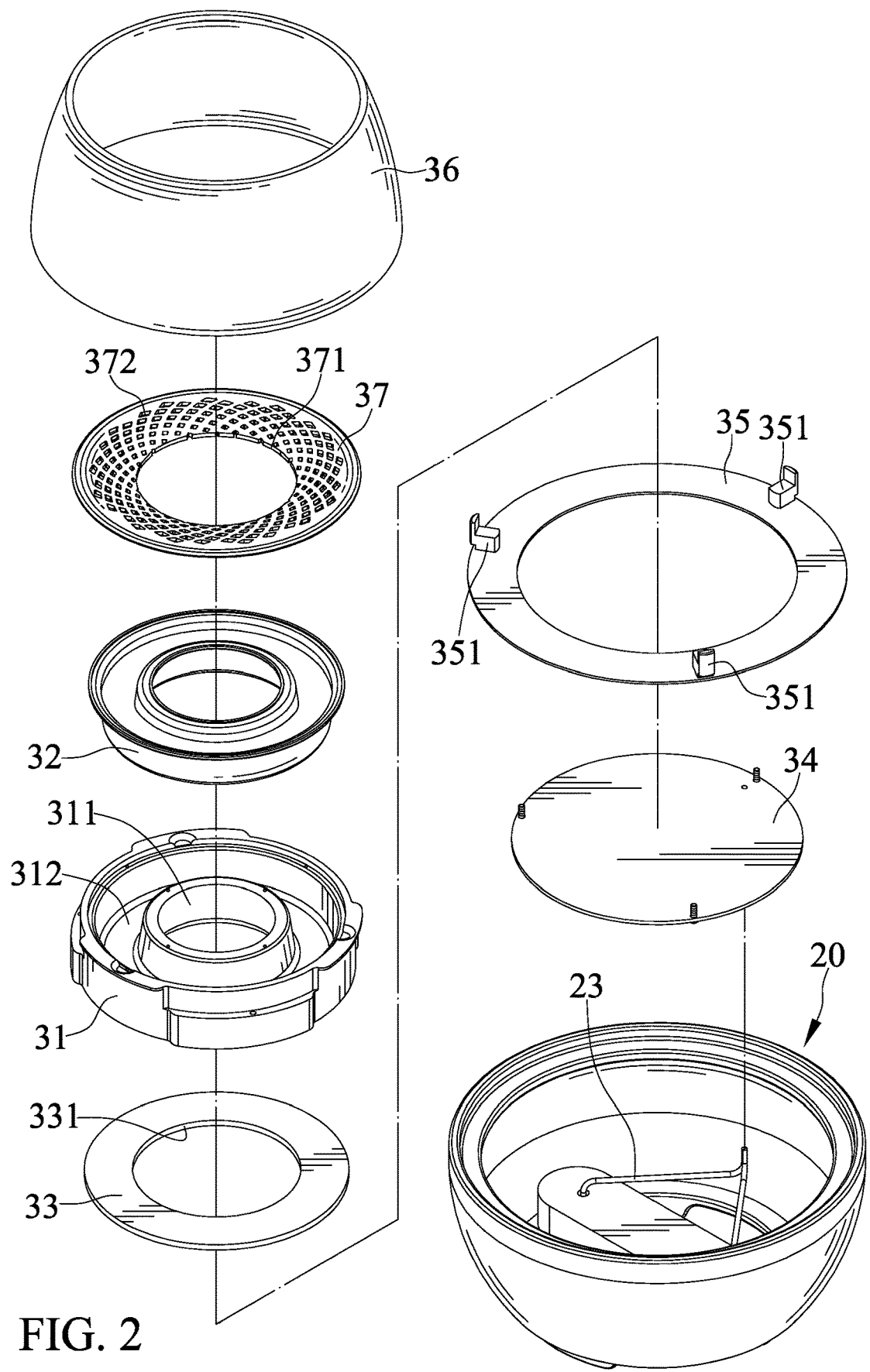
FIG. 2 is an exploded, perspective views of the electric heating fragrance diffuser of FIG. 1.
Figure 3:
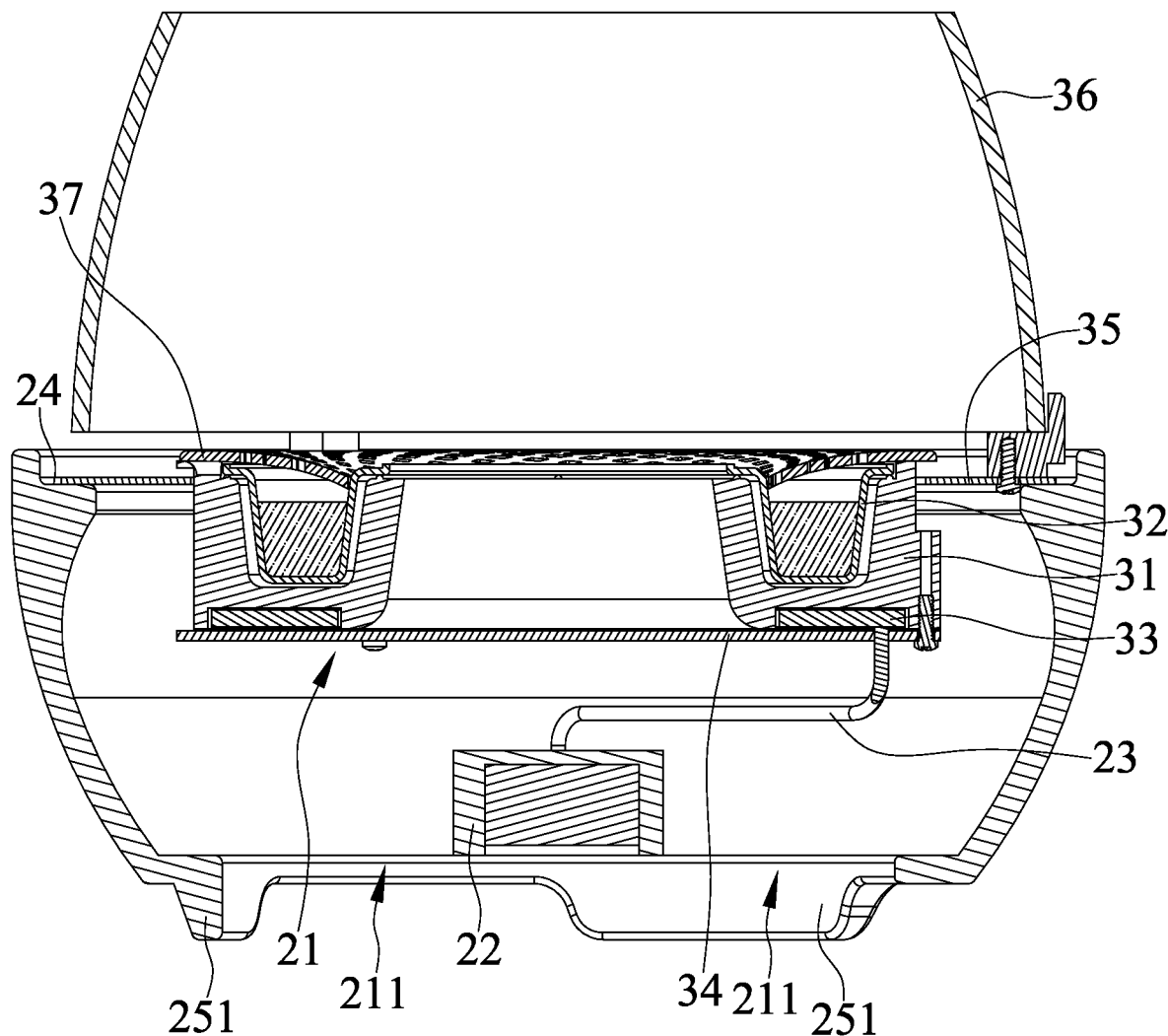
FIGS. 3 and 4 are cross-sectioned views of the electric heating fragrance diffuser of FIG. 1.
Figure 4:
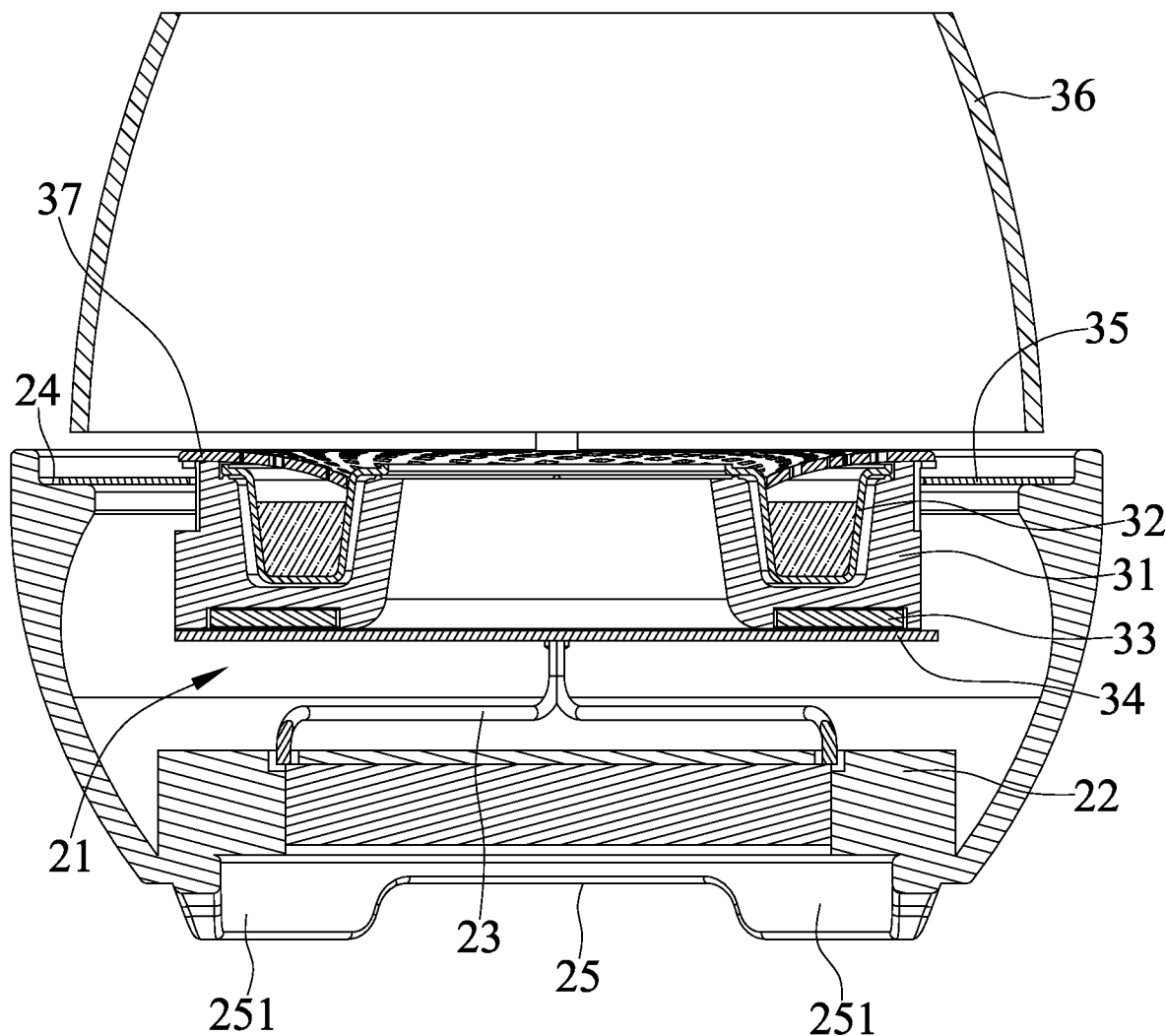

FIGS. 1-4 show an electric heating fragrance diffuser 10 of an embodiment according to the present invention. The electric heating fragrance diffuser 10 includes a body 20 and a fragrance diffusing device 30.

The body 20 is hollow and provided with an accommodating space 21 inside, and a power source 22 and an electric wire 23 are arranged in the accommodating space 21. The power source 22 can be internal or external and may include a battery, a battery set, a rechargeable battery, and a USB power supply.

The fragrance diffusing device 30 includes a fragrance holder 31, a fragrance box 32, and an electric heating plate 33. The fragrance holder 31 is disposed in the accommodating space 21 and defines upper and lower edges in a vertical direction. The fragrance holder 31 is provided with a first hole 311 communicating with upper and lower edges of the fragrance holder 31. The upper edge of the fragrance holder 31 is recessed with a fragrance groove 312 surrounding the first hole 311. The fragrance box 32 is detachably arranged in the fragrance groove 312. The electric heating plate 33 is connected to the lower edge of the fragrance holder 31 and provided with a second hole 331 aligned with the first hole 311.

The fragrance diffusing device 30 is provided with a bottom plate 34 securely connected to the lower edge of the fragrance holder 31. The electric heating plate 33 is disposed between the fragrance holder 31 and the bottom plate 34.

The body 20 defines upper and lower edges in a vertical direction. The upper edge of the body 20 is provided with a top face 24 connected to the accommodating space 21. The fragrance diffusing device 30 includes a supporting frame 35 mounted around the fragrance holder 31. An outer periphery of the supporting frame 35 abuts against the top face 24.

The supporting frame 35 defines upper and lower edges in a vertical direction. The upper edge of the supporting frame 35 is provided with a plurality of lugs 351. The fragrance diffusing device 30 includes a windshield 36 abutted against the plurality of lugs 351 and not in contact with the body 20 and the fragrance holder 31.

The fragrance diffusing device 30 includes a top cover 37 connected to the upper edge of the fragrance holder 31. The top cover 37 is provided with a third hole 371 aligned with the first hole 311 and a plurality of aeration holes 372 aligned with the fragrance groove 312.

The lower edge of the body 20 is provided with a bottom face 25 connected to the accommodating space 21 opposite to the top face 24 and adjacent to the power source 22. An end of the accommodating space 21 connecting with the bottom face 25 forms two air holes 211 respectively located at two opposite sides of the power source 22. The bottom face 25 is convexly provided with a plurality of feet 251 in a direction opposite to the top face 24.

The power source 22 is adapted to set battery for supplying power to the electric heating plate 33 via the electric wire 23. The electric heating plate 33 can heat the fragrance holder 31 and to facilitate the fragrance substance in the fragrance box 32 to emit fragrance safely and efficiently. Thus, the electric heating fragrance diffuser 10 can provide fragrance in an electrothermal manner through the above-mentioned structure.

Although specific embodiments have been illustrated and described, numerous modifications and variations are still possible without departing from the scope of the invention. The scope of the invention is limited by the accompanying claims.

The invention claimed is:

1. An electric heating fragrance diffuser comprising:
a body being hollow and provided with an accommodating space inside, and wherein a power source and an electric wire are arranged in the accommodating space; and
a fragrance diffusing device including a fragrance holder, a fragrance box, and an electric heating plate, wherein the fragrance holder is disposed in the accommodating space and defines upper and lower edges in a vertical direction, wherein the fragrance holder is provided with a first hole extending through and communicating with upper and lower edges of the fragrance holder, wherein the upper edge of the fragrance holder is recessed with a fragrance groove surrounding circumferentially the first hole, wherein the fragrance box is detachably arranged in the fragrance groove, and wherein the electric heating plate is connected to the lower edge of the fragrance holder and provided with a second hole aligned with the first hole in the vertical direction,
wherein the fragrance diffusing device is provided with a bottom plate securely connected to the lower edge of the fragrance holder, and wherein the electric heating plate is disposed between the fragrance holder and the bottom plate,
wherein the body defines upper and lower edges in the vertical direction, wherein the upper edge of the body is provided with a top face connected to the accommodating space, wherein the fragrance diffusing device includes a supporting frame mounted around the fragrance holder, and wherein an outer periphery of the supporting frame abuts against the top face, and
wherein the supporting frame defines upper and lower edges in the vertical direction, wherein the upper edge of the supporting frame is provided with a plurality of lugs, and wherein the fragrance diffusing device includes a windshield abutted against the plurality of lugs and not in contact with the body and the fragrance holder.

2. The electric heating fragrance diffuser as claimed in claim 1, wherein the fragrance diffusing device includes a top cover connected to the upper edge of the fragrance holder, and wherein the top cover is provided with a third hole aligned with the first hole and a plurality of aeration holes aligned with the fragrance groove.

3. The electric heating fragrance diffuser as claimed in claim 1, wherein the lower edge of the body is provided with a bottom face connected to the accommodating space opposite to the top face and adjacent to the power source, wherein an end of the accommodating space connecting with the bottom face forms two air hole respectively located at two opposite sides of the power source, and wherein the bottom face is convexly provided with a plurality of feet in a direction opposite to the top face.

* * * * *